United States Patent [19]

Rowley

[11] Patent Number: 5,496,800
[45] Date of Patent: Mar. 5, 1996

[54] GROWTH INHIBITORY FACTOR FROM UROGENITAL SINUS

[75] Inventor: David R. Rowley, Houston, Tex.

[73] Assignee: Baylor College of Medicine, Houston, Tex.

[21] Appl. No.: 928,867

[22] Filed: Aug. 11, 1992

Related U.S. Application Data

[63] Continuation-in-part of Ser. No. 240,171, Sep. 2, 1988, Pat. No. 5,193,334.

[51] Int. Cl.$^6$ .............................. A61K 38/00; C07K 2/00; C12P 21/00; G01N 33/53
[52] U.S. Cl. ................ 514/12; 514/21; 530/324
[58] Field of Search ............................ 435/240.2; 514/2, 514/21, 908, 12; 530/324

[56] References Cited

U.S. PATENT DOCUMENTS

| | | |
|---|---|---|
| 1,163,538 | 12/1915 | Hieatzman et al. . |
| 1,651,770 | 12/1927 | Hartmann . |
| 1,690,932 | 4/1928 | Hartmann . |
| 3,008,878 | 11/1961 | Keck . |
| 3,409,605 | 11/1968 | Florini . |
| 3,867,363 | 2/1975 | Hansen . |
| 3,901,870 | 8/1975 | Haupt et al. . |
| 4,108,849 | 8/1978 | Thomas . |
| 4,510,131 | 4/1985 | Donahoe et al. . |
| 4,708,948 | 11/1987 | Iwata et al. . |
| 5,196,334 | 3/1993 | Rowley ........................ 514/2 |

OTHER PUBLICATIONS

Johnson et al., *Cancer Treatment Reviews*, 2, 1–31, 1975.
Cunha, G. R., et al. Cell Differentiation 17:137–148 (1985).
Lasnitski, I., *Animal Cell Culture* (Freshney, R. I. ed., IRL Press, 1986) pp. 149–181.
Rowley, D. R., In Vitro Cell Dev. Biol. 28A:29–38 (1992).
Pretlow, T. G., et al., Cancer Research 51:3814–3817 (1991).
Harel, et al., Journal of Cellular Physiology 119:101–106 (1984).
Hsu, et al., Proc. Natl. Acad. Sci. USA 81:2107–2111 (1984).
Roberts, et al., Proc. Natl. Acad. Sci. USA 82:119–123 (1985).
Rowley, et al., Cancer Research 47:2955–2960 (1987).
Sporn, et al., Science 233:532–534 (1986).
Steck, et al., The Journal of Cell Biology 92:523–523 (1982).
Wang, et al., TIBS 11:24–26.
Wells, et al., Journal of Cellular Physiology 117:148–154 (1983).
Konig, et al., Urological Research 15:145–149 (1987).
Dai & Gupta, J. Biological Chemistry, 265(32):19871–19877 (1990).
Ijzermans & Marquet, Immunobiol, 179:456–473 (1989).
Quelle & Wojchowski, J. Biol. Chem. 266(1):609–614 (1991).
Ulich, et al., Experimental Hematology, 19:29–34 (1991).
Johnson, et al., Cancer Treatment Reviews 2:1–31 (1975).
Baird, et al., J. Cell Biochem Suppl. vol. O, No. 11, Part A, p. 50 (1987).
Rowley, D. R., Mol. and Cellular Biol. of Prostate Cancer (Karr, J. P., ed., Plenum Press, N.Y., 1991).
Rowley, D. R., Endocrinology 131:471–478 (1992).
Kimchi, A., et al., Science 240:196 (1988).

*Primary Examiner*—Jill Warden
*Assistant Examiner*—Lynn Touzeau
*Attorney, Agent, or Firm*—Baker & Botts

[57] ABSTRACT

A process is provided for purifying Urogenital Sinus Derived Growth Inhibitory Factor (UGIF) from embryonic tissue which comprises chromatographing medium from cultures or culture-derived spheroids of embryonic tissue derived from the urogenital sinus by gel filtration chromatography. Further purification by reverse phase high pressure liquid chromatography is also demonstrated. The UGIF is obtained in 70-fold to 8000-fold purification over the conditioned medium. A UGIF composition of matter is also provided, as is a method for treating neoplasia with UGIF.

6 Claims, 10 Drawing Sheets

- ◆ O.D AT 280 NM
- ▫ (3)H THYMIDINE INCORPORATION 1/CPM (X10(−5))

GROWTH INHIBITORY FACTOR FROM UROGENITAL SINUS

REFERENCE TO RELATED APPLICATION

This application is a continuation-in-part of Application Ser. No. 07/240,171, filed on Sep. 2, 1988, now U.S. Pat. No. 5,193,334.

FIELD OF THE INVENTION

The present invention relates to urogenital sinus derived growth inhibitory factor, methods for its purification and its use in the inhibition of selected tumors or selected tumor cell growth.

DESCRIPTION OF THE PRIOR ART

The morphogenesis and cytodifferentiation of many tissues during embryogenesis is a result of interactions between stroma and epithelium. It has been postulated that local humoral factors from stroma act to induce morphogenesis. The induction of epithelial phenotype by stroma has been studied in a variety of tissues, including mammary gland, eye, skin, stomach, lung and prostate. At least some of these inductive effects have been shown to be produced by diffusible factors produced by the stroma.

The fetal urogenital sinus differentiates into the mature prostate gland as a result of tissue-tissue interactions. Specifically, the mesenchyme (stroma) acts to induce the differentiated phenotype of the apposing epithelium. The induction of the epithelial differentiated state by the stroma has been shown by Cunha et al. (for reviews see *Cell Differentiation* 17:137–148, 1985). It has been shown that during a specific window of time (day 17–19 in the fetal rat and mouse), the stroma induces the epithelium to express the normal differentiated state. Additionally, heterotypical tissue-tissue recombinant studies have demonstrated that urogenital sinus stroma at this stage can induce both fetal and adult bladder epithelium to that of a prostate-type epithelium. While bladder epithelium cells do not normally possess androgen receptors or antigens specific for prostate tissue, the induced epithelium demonstrated not only the morphology of a normal prostate epithelium, but also expressed androgen receptors and prostate specific antigens. Epithelial cells from mice with Testicular Feminization Syndrome (Tfm) do not respond to androgen hormone. However, when such Tfm epithelium was incubated as heterotypical tissue-tissue recombinants with normal urogenital sinus stroma, normally differentiated, prostate-appearing epithelium was produced which responded to androgen stimulation. Such studies point to the potent nature of the inductive influence of the urogenital sinus stroma. Currently, although little is known regarding the mechanisms of stromal-epithelial interactions in the developing urogenital sinus, the existence of certain paracrine acting factors which regulate growth and differentiation of epithelium in a local environment has been postulated.

The prostate gland develops from the urogenital sinus during embryogenesis. The prostate epithelium is induced by the mesenchyme (stroma) of the urogenital sinus. In tissue recombination studies, fetal rat urogenital sinus has been shown to induce both fetal and adult normal bladder epithelial cells to express a prostate-specific phenotype.

Additionally, factors produced by normal tissues have been shown to regulate the growth and differentiation of neoplastic cells. This invention teaches that urogenital sinus tissue, and more specifically, a factor derived from urogenital sinus tissue, can be used to alter the phenotype of cells, including, but not limited to, normal bladder epithelial and bladder carcinoma cells and can be used to treat tumors or selected tumor cell growth or neoplastic conditions. "Normal" as used herein refers to those tissues, cells, organs or organisms that are commonly recognized by those of ordinary skill in the art as possessing, in whole or in part, a non-diseased state. Among the alterations caused by the urogenital sinus tissue is the inhibition of cell proliferation, the stimulation of protein secretion and alterations in cell morphology.

The characterization and purification of urogenital sinus derived inhibitory factor (UGIF) from urogenital sinus organ explants and derived fibroblastoid monolayers by the inventor represents a major advancement in understanding the role of such factor(s) in urogenital sinus development.

Because of the great applicability of UGIF and the need to provide a substantially purified UGIF, there is a need for a method of purification for, and substantially purified fractions of this material.

These and other disadvantages of the prior art are overcome by the present invention, and a new urogenital sinus-derived factor is provided, as well as methods for using this factor in treating selected conditions such as, but not limited to, conditions related to the urogenital system and selected tumors or tumor cell growth.

SUMMARY OF THE INVENTION

It is therefore an object of the present invention to provide a substantially purified UGIF.

It is another object of the invention to provide compositions comprising UGIF bioactive fractions.

It is another object of the invention to provide a method of inhibiting the growth of tumors and tumor cells.

Yet another object of the invention is to provide improved methods of treating certain carcinomas.

It is a further object of the invention to provide improved methods and compositions for treating urogenital disorders.

These and other objects of the invention, as will hereinafter become more readily apparent, have been attained by providing:

A process for purifying biologically active UGIF from tissue which comprises:
- (a) incubating urogenital sinus tissue in an appropriate aqueous culture medium for a time sufficient to synthesize and secrete UGIF from said tissue into said medium,
- (b) dialyzing the medium obtained in step (a) and collecting said UGIF,
- (c) chromatographing said UGIF obtained from step (b) on a gel filtration column and collecting fractions containing biologically active UGIF,
- (d) chromatographing said UGIF obtained from step (c) with a high performance (pressure) liquid chromatography system using reverse phase column(s) and collecting fractions containing biologically active of UGIF.

Other objects of the invention have also been attained by providing:

A composition comprising UGIF derived from tissue having an activity of at least 1 as measured by the UGIF units assay, being substantially free of albumin and being about 70–8,000 fold enriched in UGIF activity over the conditioned medium which was the starting material for the purification.

Yet other objects of the invention have been attained by providing a composition comprising UGIF derived from tissue having an activity of at least 1 as measured by the UGIF units assay; being substantially free of albumin and of proteinaceous material; having a molecular weight of 10,000–20,000 Daltons; and being about 70–8,000 fold enriched in UGIF activity over the conditioned medium starting material.

Other objects of the invention have been attained by providing:

The substantially pure polypeptide urogenital sinus derived growth factor having a specific activity greater than 70 units per mg protein as measured by the UGIF units assay test;

An in vitro method of inhibiting the growth of cells containing putative UGIF receptors which comprises contacting said cells with a growth suppressing amount of the UGIF composition;

A method of suppressing the growth of cancer cells which comprises contacting said cells with a growth suppressing amount of UGIF;

A method of suppressing the growth of cancer cells wherein said cancer cells are prostatic cancer, breast cancer, lung cancer, cervical cancer, or any neoplasia (cancer) containing UGIF-responsive cells;

A method of treating conditions related to hyperplasia of urogenital sinus derived cells which comprises contacting said cells with a growth suppressing amount of UGIF;

A method of treating conditions related to hyperplasia of urogenital sinus derived cells wherein said conditions are selected from the group consisting of benign prostatic hyperplasia, prostatitis, and testicular feminization syndrome;

A continuous cell line which produces the urogenital sinus derived growth factor;

Spheroids derived from the continuous cell line;

A continuous cell strain developed from the Spheroids;

A method of producing UGIF using the cells, spheroids and/or continuous cell strain; and A method of assessing UGIF activity comprising
a) seeding cells in a multi-well culture plate with medium;
b) incubating the cells and medium for about 24 hours;
c) removing said medium containing the sample;
d) incubating the cells for about 22 hours;
e) adding about 2 μCi/ml [$^3$H]thymidine to each well;
f) incubating for about 2 to 3 hours;
g) stopping [$^3$H]thymidine incorporation by adding a mixture of methanol:acetic acid (3:1, volume/volume ratio); and
h) measuring amount of [$^3$H]thymidine incorporated.

These and other advantages of the present invention will become apparent from the following detailed description.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
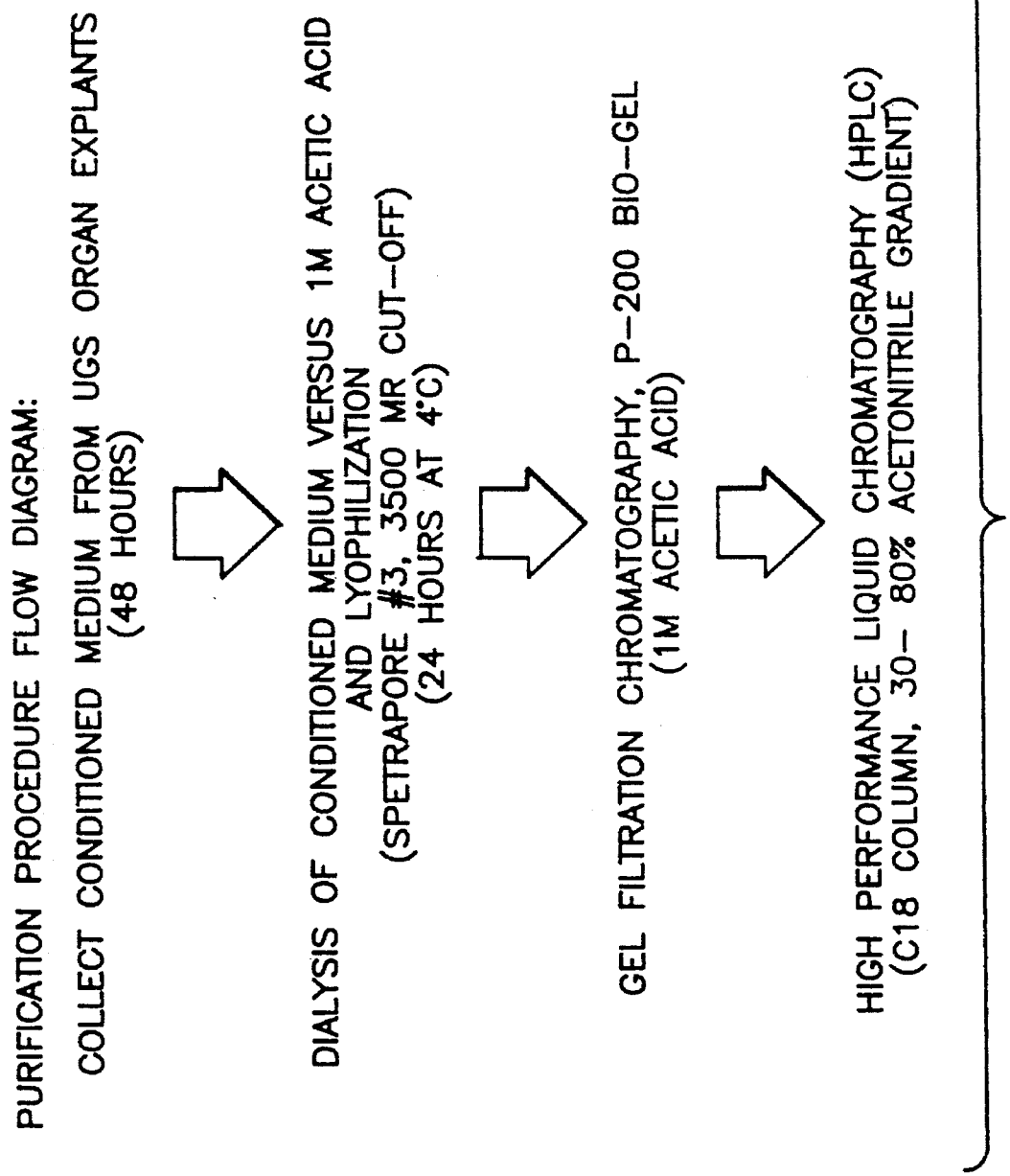
FIG. 1 shows the sequential steps in the purification of urogenital sinus derived factor.

The present invention provides a process for the purification of UGIF from urogenital sinus tissue.

The materials prepared at different stages of the process of the present invention are all distinct embodiments of the present invention, and they can all be used for the treatment of selected tumors in animals. The materials are particularly useful for the treatment of selected carcinomas in animals.

The process of the invention comprises excising urogenital sinus tissue from the fetal animals and thereafter incubating said urogenital sinus in culture medium at physiological temperatures (25°–37° C., preferably 37° C.). The medium should contain amino acids, vitamins and isotonic salts. Examples of incubation media include DMEM, Basal Media Eagle's, CMRL 1066 or MEM, all of which are readily obtainable and known to those possessing ordinary skill in the art.

Conditioned medium from the organ explants is preferably collected each 48 hours, but is not limited to this collection schedule. Incubation of medium longer than 48 hours per sequential collection may not increase the units of assayable UGIF activity in the medium.

UGIF may be purified from any source, such as, conditioned medium by chromatographic procedures. Any procedures may be utilized known to those of skill in the art which are capable of isolating a protein having the characteristics of UGIF, i.e., a molecular weight of 10,000–20,000 Daltons, acid stability, stability at 80° C. for at least 10 minutes, and having the biological effects of inhibition of cell proliferation of cell lines NBT-II, Mv 1 Lu, A-549, Y-79, NRK and primary fibroblasts derived from fetal rat urogenital sinus.

In one embodiment, UGIF may be purified from medium which has been "conditioned" by incubation with organ explants of fetal rat urogenital sinus (conditioned medium, CM). The CM, containing approximately 70 units of UGIF activity per mg protein may be subject directly to chromatographic separation to obtain UGIF.

In another embodiment, UGIF may be purified from medium from cultured cells such as mesenchymal-type cells or cell products such as cultured cells or cultured-cell products. These include, but are not limited to, a U4F mesenchymal cell line, U4F spheroids, or a U4F1 cell strain.

Alternatively, the conditioned medium may be acidified to precipitate acid insoluble proteins prior to application of the soluble fraction to the chromatographic column. Preferably, the acidification is achieved by dialysis of the CM with acid for 24 hours at 4° C. Most preferably, the CM is dialyzed against 1M acetic acid.

The dialysis of the conditioned medium with acid, preferably 1M acetic acid, for 24 hours at 4° C. results in the presence of precipitated protein and soluble protein in the resulting dialyzed medium. Assayable UGIF activity is obtained and recovered in the soluble fraction.

The UGIF containing solution is further purified by chromatographic methods. Preferably, the UGIF is concentrated prior to application to a chromatographic column. This concentration step may be omitted. However, application of concentrated UGIF to the columns provides larger yields and better recovery of UGIF. The UGIF concentration may be accomplished by any means known to those of skill in the art such as lyophilization or ultrafiltration. Preferably, the UGIF preparation is concentrated by lyophilization to dryness.

The UGIF preparation is next subject to chromatographic purification. Preferably, the first chromatographic step is carried out after the material obtained from dialysis is lyophilized to dryness. The dried sample is resolubilized in acid conditions, preferably, but not limited, to 1M acetic acid. The UGIF preparation is next subject to chromatographic purification. Preferably, the UGIF sample is chromatographed on a gel filtration column and separated from other proteins on the basis of molecular weight and/or molecular shape and size. The preferable gel filtration medium is Bio-Gel P-200 (Bio Rad Corp., Richmond, Calif., USA), however any gel filtration matrix that separates proteins on the basis of size and/or shape could be used.

After this step, the eluted fractions are assayed for UGIF biological activity using a biological assay such as those below described. Fractions containing significant units of UGIF activity are pooled and lyophilized to dryness.

The resulting lyophilized material is resolubilized in a solution compatible with a high performance liquid chromatographic reverse phase (HPLC) column. Alternatively, UGIF concentrated by any other means is put into an HPLC compatible solution. The preferable solubilizing solution is 1% trifluoroacetic acid, but other suitable solutions will be known to those of skill in the art. Any solubilizing buffer which is compatible with HPLC is acceptable. The preferable reverse phase column is one with a C18 configuration, yet is not limited to such. Any matrix which separates proteins based on their hydrophobic nature is acceptable.

The HPLC column may alternatively be selected from the group consisting of BioGel TSK columns which have phenyl group columns, C4 columns such as Hi-Pore RP304, and C18 columns such as Hi-Pore 318, Bio-sil ODS-10 and ODS-55 or any other equivalent column.

After loading onto the HPLC column, proteins including UGIF are differentially eluted with any solvent or solution suitable to reverse the binding of proteins to said column. The preferable solvent is a 30%–80% gradient of acetonitrile added to the column at a rate of 0.5% change per minute.

After this step, the eluted fractions are assayed for UGIF biological activity using a biological assay. Fractions containing UGIF activity are dried by exposure to heat in a vacuum dryer. Exposure to 70°–90° C. for 10 minutes is suitable; alternatively the fractions are allowed to air dry.

These fractions can be stored at −20° C. for indefinite periods. The purification of UGIF by this procedure is indicated in Table I.

TABLE I

| | Purification of UGIF: | | | |
|---|---|---|---|---|
| Step | Protein (mg) | UGIF Units | Units/ Protein | Fold Purification |
| CM | 177 | 12400 | 70 | 1 |
| Dialyzed CM | 172 | 12400 | 72 | 1 |
| P-200 Peak | 2.4 | 11861 | 4942 | 70 |
| HPLC Peak | 0.015 | 8324 | 554933 | 7928 |

The data in Table I summarizes the results obtained from a starting volume of original urogenital organ explant conditioned medium of 50 ml.

It is fully anticipated that additional purification modifications will lead to the complete purification of UGIF to homogeneity.

Once the UGIF is sufficiently homogenous, the amino acid sequence can be determined.

In addition, the UGIF of the present invention can be used to develop polyclonal and monoclonal antibodies specific for UGIF, which can be used to develop immunoassays for UGIF. Such assays could be used clinically to assay for UGIF in human or animal tissues and/or fluids. Additionally, the UGIF antibodies can be utilized to further purify UGIF utilizing affinity techniques known to those of skill in the art. UGIF antibodies can also be used to neutralize UGIF biological activity should excess UGIF activity be associated with a disease state or otherwise abnormal condition.

Once the amino acid sequence is determined, oligonucleotides may be synthesized and the antibody probes and synthetic oligonucleotides used to clone the cDNA and genomic genes which code for UGIF. The clones will be used to genetically engineer microbiological organisms or other cells or cell types to produce UGIF. Such genetically engineered organisms will be used to produce large quantities of UGIF for clinical and/or research purposes.

The determination of UGIF biological activity in aliquots from each aforementioned step is determined by either or both of the following assays. The mink lung epithelial (Mv 1 Lu cell) miniassay utilizes the inhibition of tritiated thymidine ([$^3$H]thymidine) incorporation into DNA effected by exposure of the cells to UGIF. For this assay, Mv 1 Lu cells are seeded in tissue culture wells ($6.0 \times 10^3$ cells/well of a 96 well dish) and exposed to samples of UGIF solubilized in the appropriate culture medium. After exposure of the cells to the UGIF for 20–22 hours, the Mv 1 Lu cells are exposed to tritiated thymidine (2 μCi/ml) for 2–3 hours. The cells are then fixed in an acid-methanol fixative (methanol:acetic acid, 3:1, volume/volume ratio), washed with methanol followed by 5% TCA, followed by methanol, extracted with 200 μl of 1N NaOH, neutralized with the same volume of 1N HCl and radioactivity is determined by scintillation counting.

The second assay is the Y-79 cell suspension assay. The principles of this assay are identical to the miniassay described above with the exception that Y-79 cells are used instead of Mv 1 Lu cells. Y-79 cells, a human retinoblastoma cell line, grow in suspension rather than in monolayers. Accordingly, this assay requires one day less for completion.

In addition, this assay precludes the potential interpretation that growth inhibition might be due to endogenous levels of transforming growth factor type beta (TGF-β), since Y-79 cells are negative for TGF-β receptors and do not respond to TGF-β. Y-79 cells seeded at $4 \times 10^4$ cells per ml/well in Bfs medium. The wells are exposed to UGIF active samples for 22 hours. [$^3$H]thymidine is added at 2 μCi/ml for 2–3 hours. The cells are collected from the tissue culture well, TCA precipitated, washed extensively with ethanol on filters (AH-539, 2.4 cm) in a sampling manifold, and the filters are scintillation counted for radioactivity.

Although these assays are preferable, any bio-assay which distinguishes UGIF samples based on the ability to inhibit cell growth (nucleotide incorporation and/or cell number) is suitable for measuring UGIF biological activity. In addition, since UGIF acts to alter cell morphology and affects the secretion of newly synthesized proteins, any assay which would distinguish experimental samples based on these properties would be acceptable.

Figure 5:
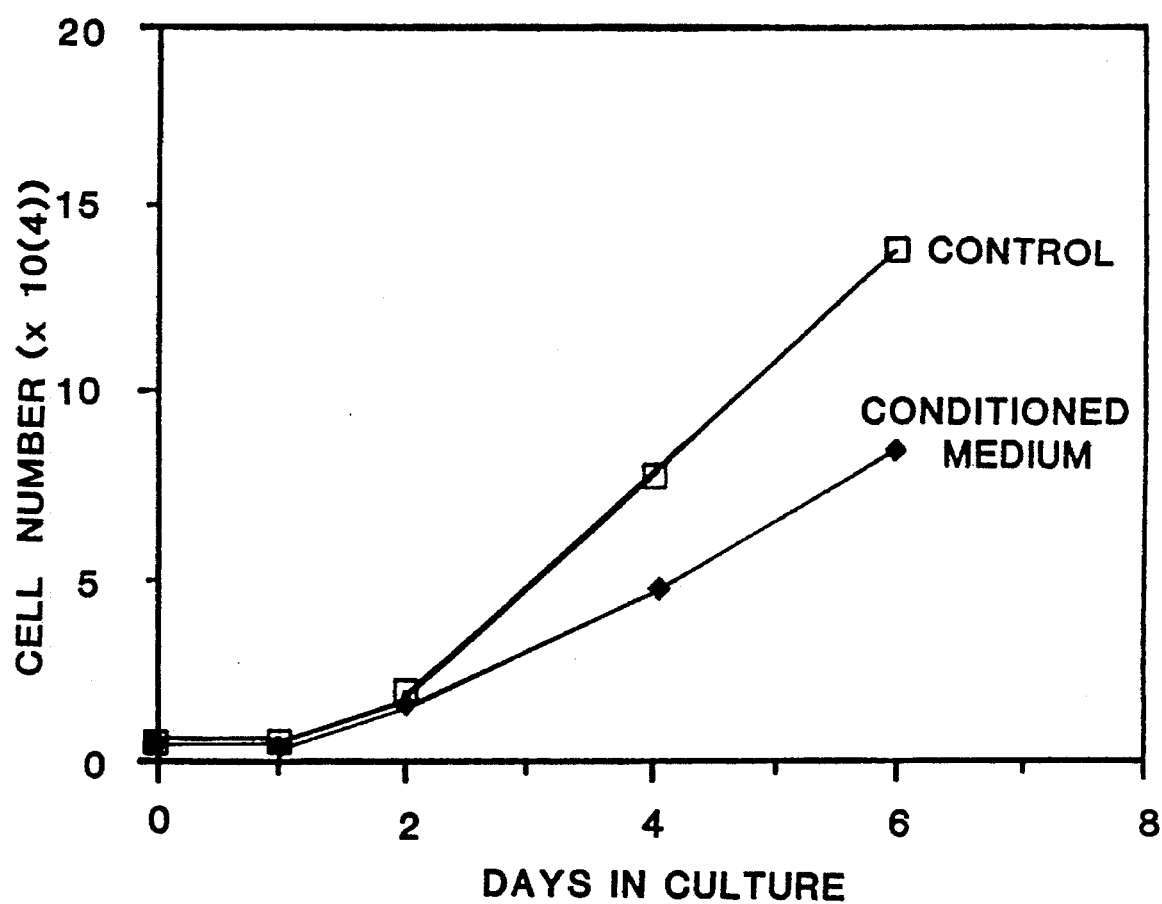
FIG. 5 demonstrates the inhibitory effects of UGIF on cell proliferation.

The purified active UGIF-rich fractions of the present invention exhibit profound effects on the inhibition of growth or the selective destruction of transformed cells and tumors (FIG. 5). UGIF inhibits the growth of several cell lines of varied tissue origins and from at least three species of distant phenotypic and genotypic profiles. Table II demonstrates that UGIF inhibits normal and transformed cells and cell lines from rat bladder carcinoma (NBT-II), mink lung (Mv 1 Lu), rat urogenital sinus (normal fibroblasts), normal rat kidney (NRK), human lung carcinoma (A-549), human cervical carcinoma (HeLa), and human retinoblastoma (Y-79). Accordingly UGIF appears to affect a diverse and varied types of cells and/or tissues from several species.

TABLE II

| Cell lines inhibited by UGIF | | |
|---|---|---|
| Name: | Tissue Derived From: | Cell Type: |
| NBT-11 | Rat Bladder Carcinoma | Transitional Cell |
| Mv 1 Lu | Fetal Mink Lung | Epithelial |
| A-549 | Human Lung Carcinoma | Epithelial |
| Y-79 | Human Retinoblastoma | Retinoblastoma |
| HeLa | Human Cervix Carcinoma | Epithelial |
| NRK | Normal Rat Kidney | Fibroblast |
| UGS Fibroblasts | Fetal Rat Urogenital Sinus | Fibroblast |

*All cell lines were inhibited by >50% ([$^3$H]thymidine incorporation assays) (30% volume/volume CM)

The active UGIF-rich fractions of the invention are administered to animals, including humans or other mammals, animal cells, including human cells, in tissue culture or used in an assay system to cells such as, but not limited to, rat carcinoma, human carcinoma or retinoblastoma.

Figure 4:
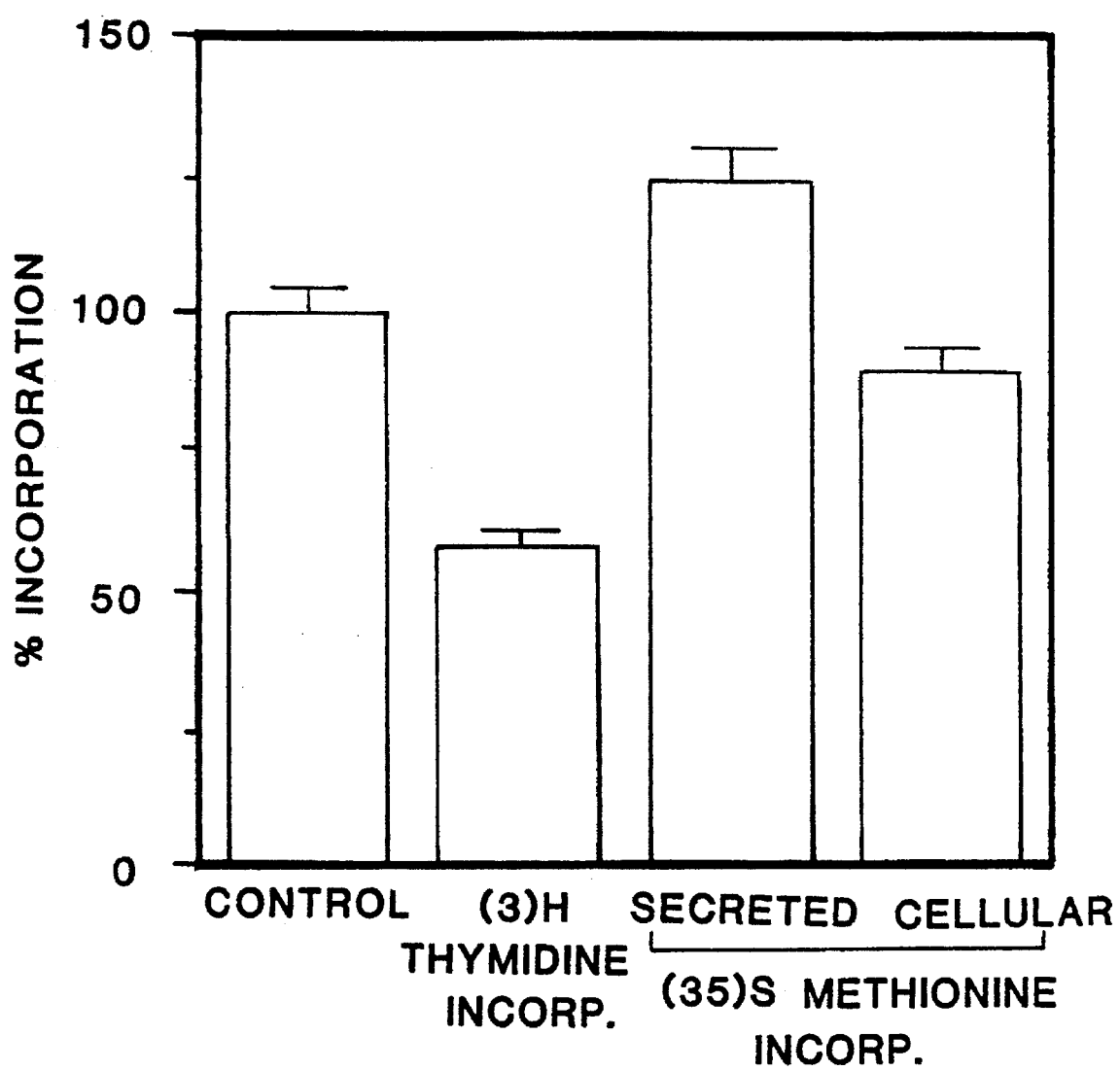
FIG. 4 demonstrates the stimulation of protein synthesis and secretion by UGIF.
Figure 6A:
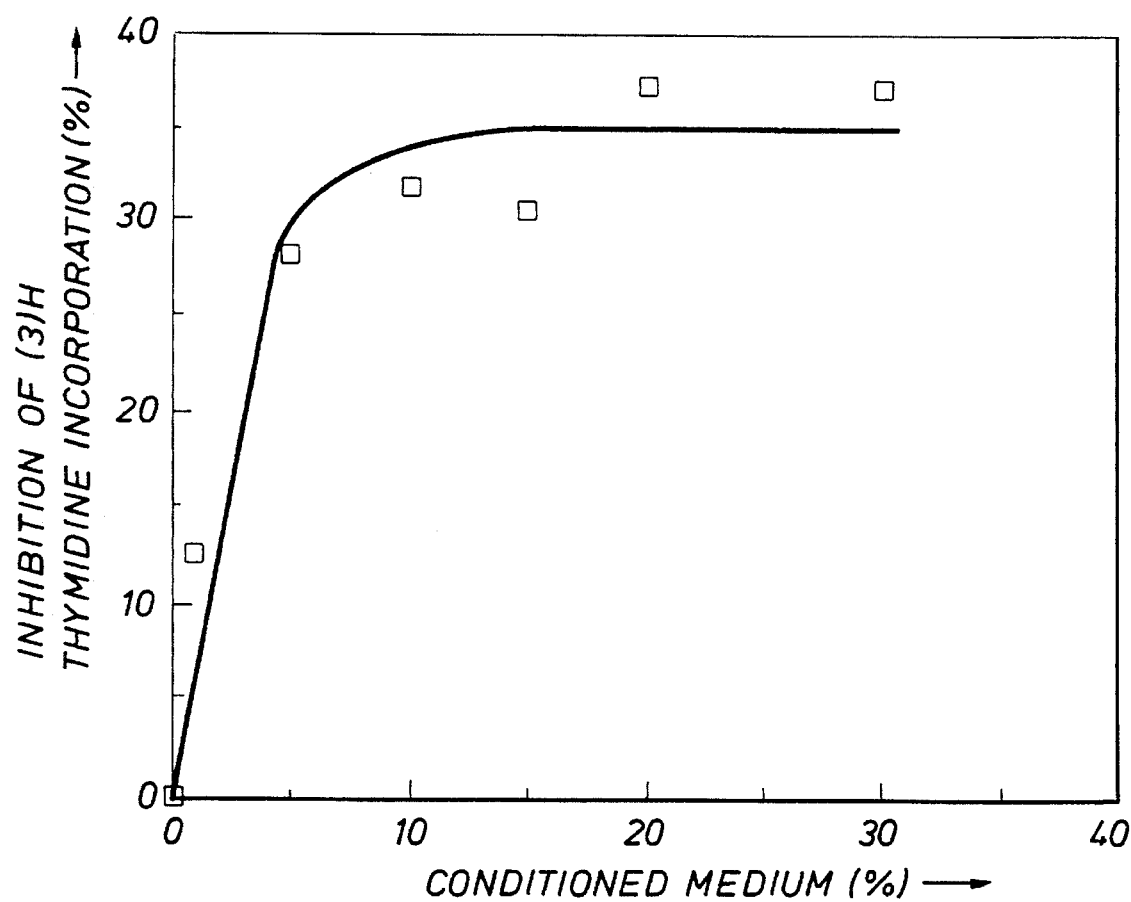
FIG. 6 demonstrates the dose-response effects of UGIF on the [$^3$H]thymidine incorporation in Y-79 cells.
Figure 6B:
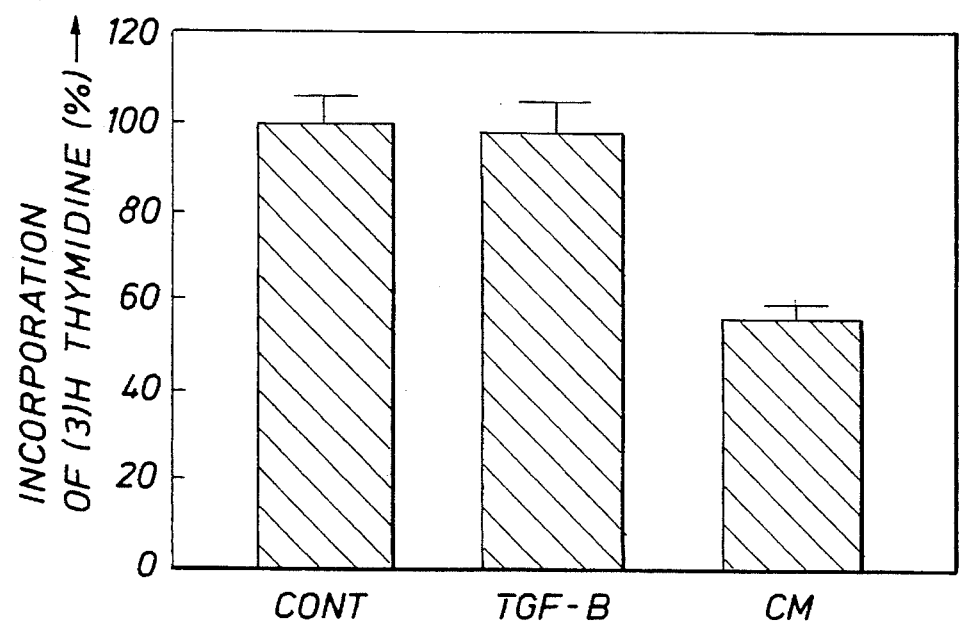
Figure 7A:
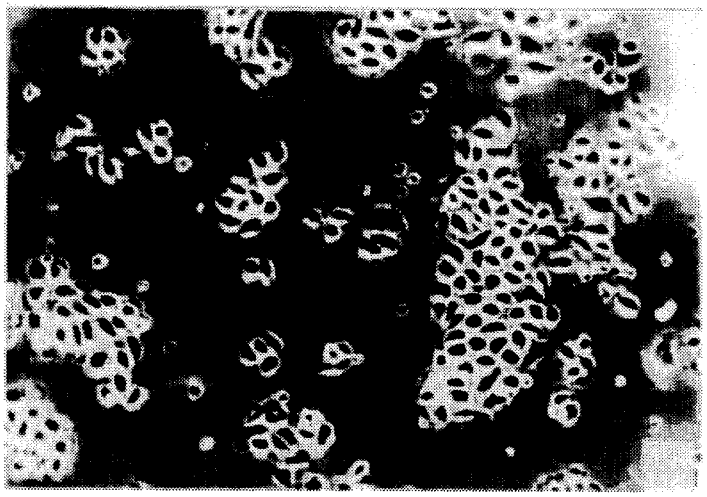
FIGS. 7A, 7B and 7C demonstrate the effects of UGIF on cell morphology.
Figure 7B:
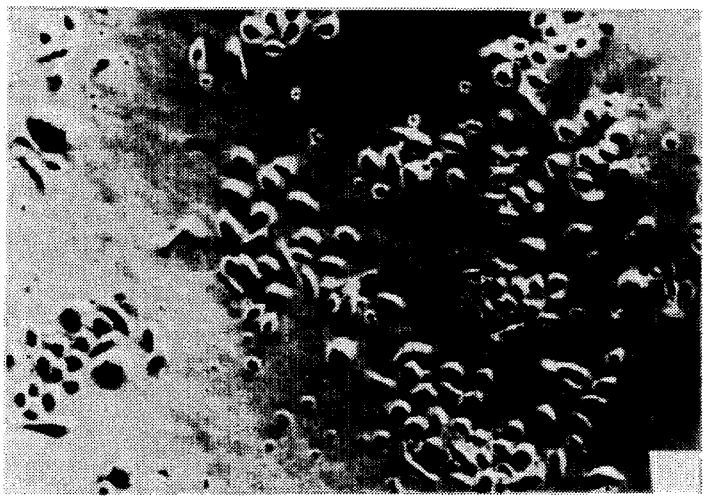
Figure 7C:

The active UGIF-rich fractions from each step of the purification protocol of the present invention exhibit profound effects on the inhibition of growth of transformed cells (FIG. 4). The active UGIF-rich fractions of the invention are administered to a wide variety of animal and human cells in tissue culture at varying concentration levels. UGIF is active at low concentrations (nM levels) and cell cultures demonstrate a linear, dose-response curve to UGIF administration (FIG. 6). Cell cultures demonstrate a saturable response to increased concentrations of the UGIF of the present invention. In addition to altering cell growth, UGIF affects the secretion of proteins and alters cell morphology (the cells become larger and more distended) as shown in FIGS. 4 and 7, respectively).

The units of UGIF biological activity are determined by analysis of data generated with the biological assay using cells in culture as described previously. For determination of UGIF units of activity, the following analysis of data is conducted. A standard linear curve of percent inhibition (relative to control cultures) versus percent conditioned medium added to the respective culture is generated. The conditioned medium (crude preparation) used to generate the standard curve is stored frozen in identical aliquots for use in one assay. Hence, each units assay is scored versus an identical standard curve. For the standard curve the percent conditioned medium (CM) value which produces a maximal inhibition of tritiated thymidine incorporation prior to or just at the point of saturable response to increased CM concentrations, is assigned a units score of 2. The negative control is assigned a units value of 0. The percent CM which generates one-half maximal inhibition is assigned a units value of 1. Accordingly, the experimental sample(s) being tested will produce a certain percent inhibition based on the concentration of UGIF present in the specific sample. This level of inhibition is scored versus the levels of the standard curve and a units score can be assigned to the experimental sample. Accordingly, for any specific sample to be tested, a units value of 0 through 2 will be determined. If a particular sample scores outside the sensitive range of 0–2, then an aliquot of greater volume (higher concentration of UGIF) or lower volume (lower concentration of UGIF) is re-assayed from the same sample. The units of activity in the aliquot tested are then adjusted to determine the total units present in the entire sample.

UGIF shares several physiochemical and biological properties with other known growth regulatory factors. However, there are key properties of UGIF which differentiate UGIF from other known factors. The two most closely related factors are transforming growth factor type beta (TGF-β) and fibroblast growth regulatory factors (FGRs). The similarity between these factors lies in their ability to inhibit cell growth. Both UGIF and TGF-β are heat and acid stable, but TGF-β has a molecular weight of about 25 kiloDaltons under non-reducing conditions while UGIF has a molecular weight of 10–20 kiloDaltons. The Y-79 cell line used in the suspension assay to test for UGIF activity does not respond to TGF-β and does not contain TGF-β receptors. An additional distinction is shown by the fact that TGF-β stimulates the growth of the NRK cell line (Normal Rat Kidney Cells), whereas UGIF inhibits the growth of this cell line. These lines of evidence show clearly the distinct nature of UGIF as compared to TGF-β. UGIF is distinct from the FGR factors which are heat labile and have a molecular weight of 10–13 kiloDaltons; UGIF being heat stable and having molecular weight of 10–20 kiloDaltons. For these reasons, it is clear that UGIF is distinct as compared to the FGRs.

Since most transformed cells tested to date (murine and human) have shown response to UGIF, it is likely that the UGIF receptor is ubiquitous in nature and found on many eukaryotic cells. Moreover, UGIF is probably highly conserved across species lines, since rat, mink and human cells respond in a highly similar manner. As is the case with most other growth factors, the ubiquitous nature of the receptors relates to the ubiquitous presence of the corresponding growth factor. Accordingly, it is likely that UGIF can be isolated from many types of eukaryotic tissues and/or cells. The production and isolation of UGIF is therefore not restricted to urogenital sinus tissue.

Similarly, UGIF has been shown to inhibit the growth of a wide variety of cell types from a number of different species. For this reason, administration of UGIF to an individual with carcinoma or other neoplastic diseases will provide an effective treatment for these diseases, which include, but are not limited to prostatic, breast, lung, or cervical cancer, or any neoplastic disease associated with UGIF-responsive cells.

Additionally, since UGIF activity is consistent with differentiation and diminished proliferation of normal cells, conditions related to hyperplasia of the urogenital sinus derived cells, such as the disease of benign prostatic hyperplasia (BPH), prostatitis, testicular feminization syndrome (Tfm), or any other disease or malady which affects the growth or differentiated state of the fetal, neonatal, or adult prostate gland or urogenital sinus derived tissues such as vagina and cervix in the female, will benefit from treatment with UGIF. The expression of a differentiated phenotype can be shown by a decreased proliferative rate and increased protein synthesis of secretory proteins.

In addition to the treatment of cancer related tumors in humans as well as in animals, there exists a potential use of UGIF in the treatment of other clinical manifestations dealing with abnormalities of the genitourinary system. Diseases which are manifested by a loss, lack or change in the normal tissue or cell differentiation could be treated by UGIF since this factor induces changes in cellular phenotype (state of cell differentiation) to that more suggestive of the normal phenotype. Accordingly, UGIF could be used to treat Benign Prostatic Hyperplasia (BPH) and prostatic diseases in a high proportion of aging men. Moreover, UGIF could be used to treat certain fetal and neonatal diseases such as testicular Feminization Syndrome (Tfm), as well as other developmental abnormalities which produce an altered and otherwise abnormal tissue and/or cellular phenotype in any urogenital sinus derived tissues including the female vagina and cervix. It is clear and reasonable to suggest that any disease, syndrome, or otherwise irregularity of the genitourinary system could be affected by UGIF and could be induced to a state of more normal differentiation and phenotype.

Administration of the compounds useful in the method of the present invention may be by topical, parenteral, oral, intranasal, intravenous, intramuscular, subcutaneous, or any other suitable means. The dosage administered may be dependent upon the age, weight, kind of concurrent treatment, if any, and nature of the condition being treated. The effective compound useful in the method of the present invention may be employed in such forms as capsules, liquid solutions, suspensions, or elixirs, for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

The term "individual" is meant to include any animal, preferably a mammal, and most preferably a cat, dog, cow or human.

The UGIF of the present invention including recombinant proteins and monoclonal antibodies thereto can be administered to an individual parenterally by injection, long release implants, rapid infusion, intravenously, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable liquid dosage forms include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

Generally, the dosage of UGIF protein administered to an animal will vary depending on such factors as age, condition, and whether alteration of cell/tissue differentiation or phenotype, or an inhibition of cell/tissue growth is the object of the administration, and other variables which can be readily ascertained and adjusted by one of ordinary skill in the art.

Having now generally described the invention, the same may be further understood by reference to the following examples, which are included herein for purposes of illustrating specific embodiments and are not intended to be limiting unless so expressly stated.

EXAMPLE 1

Assay of UGIF

Two procedures have been developed empirically assess UGIF activity. Both procedures are biological assays relying on the response of certain cells to UGIF as a score of activity.

A. Miniassay. This assay is referred to as the miniassay, since it is achieved with a minimum of cells in 96-well tissue culture microplates. The procedure was developed as a modification of the [$^3$H]thymidine autoradiography procedure as described by Lasnitski, I., "Organ Culture," in Freshney, R.I., ed., *Animal Cell Culture*, IRL Press, 1986: 149–181. This assay is compatible with any cell type which: (a) responds to UGIF with a decrease in [$^3$H]thymidine incorporation and; (b) is anchorage dependent, that is a cell type which attaches to the culture plate (assay 1B is designed for cells grown in suspension).

Viable cells were seeded at a density of $6.0 \times 10^3$ cells/well in a 96 well tissue culture plate (Falcon, Becton Dickinson, Oxnard, Calif., USA), with 148 μl of growth medium/well, and allowed to attach and incubate for 24 hours in a tissue culture incubator at 37° C. and 5% $CO_2$. Growth medium for this assay was medium Bfs composed of 90% Dulbeccos modification of Eagle's Minimum Essential Medium (DMEM, GIBCO, Grand Island, N.Y., USA), supplemented with 5% fetal calf serum, 5% Nu-Serum (Collaborative Research Inc., Lexington, Mass., USA), penicillin (100 units/ml), streptomycin (100 μg/ml), insulin (5 μg/ml), and testosterone (0.5 μg/ml). Although medium Bfs is the preferred media, this assay is not restricted to this particular media. Any media which is compatible with the growth and viability of the chosen responding cell type would be acceptable. After the cells were incubated for about 24 hours, the medium was supplemented with 52 μl of fresh medium containing the sample to be assayed. For liquid samples, up to 30% v/v of the final volume can be tested. Dry samples (lyophilized) may be resolubilized directly in medium Bfs. Cultures were incubated for about another 22 hours. After this incubation, about 2 μCi/ml of [$^3$H]thymidine was added to each well, and cultures were allowed to incubate for an additional 2–3 hours. [$^3$H]thymidine incorporation was stopped by the=addition of methanol: acetic acid (3 parts methanol: 1 part acetic acid) for 5 minutes at room temperature. This step acts to chemically fix the cells to the culture surface and maintains the cellular structure. The cultures were then fixed and washed further by the addition of 100% methanol (200 μl/well) for 5 minutes at room temperature. The plates were then washed with 5% trichloroacetic acid (TCA), (200 μl/well) for 5 minutes at room temperature. The cultures were then washed an additional 3 times with 100% methanol. The TCA and methanol wash steps act to wash out all the unincorporated, free thymidine (thymidine that has not been incorporated into DNA). The methanol primarily washes out the free thymidine from the cell cytoplasm. The TCA wash is primarily to wash the free thymidine from the cell nucleus. The cultures were then extracted with 1N NaOH (200 μl/well) for 5 minutes at room temperature. This step acts to hydrolyze the cells and release all proteins and DNA in the NaOH. Aliquots (180 μl) were then removed from each well and added to scintillation vials which contained 180 μl of 1N HCl to neutralize the NaOH. This mixture was counted for radioactivity by scintillation counting. The cpm from the samples was then compared with those of the controls (wells not receiving UGIF preparations) and the percent inhibition of tritiated thymidine incorporation relative to control was determined. The inhibition of [$^3$H]thymidine incorporation was approximately 50% under these conditions, identical to that shown in FIG. 4, but varies with the dose of UGIF given. The percent inhibition may be either more or less than 50%.

The assay to determine Units of UGIF bio-activity is the same as the miniassay just described. For the Units assay, crude conditioned medium from UGS organ explant cultures was used as a standard of UGIF activity. A large volume of crude conditioned media (CM) was saved frozen in 1 ml aliquots. For each Units assay one of these identical aliquots was thawed and used as standard control. The standard CM was added to triplicate wells of cells in increasing concentrations (0–30% v/v). Previous studies have shown that with increasing concentration of CM, there was a linear correlation between % volume of CM and the % inhibition of thymidine incorporation. In addition, the response to CM was saturable, that is, above 15–20% CM the % inhibition was maximal and did not increase with increased concentration of CM. These properties were used to construct a method of analysis leading to the determination of Units of UGIF activity. The % CM value which gave 100% maximal inhibition was assigned a value of 2 Units. The % CM value which gave 50% maximal inhibition was assigned a value of 1 Unit, and 0% CM which gave 0% inhibition was assigned a Units value of 0. Each experimental sample was assigned a Units value based on a linear regression line of % inhibition versus Units as generated from the standard CM data. Therefore, the % inhibition of the unknown experimental sample was analyzed in the calculation and the Units for that specific sample was determined. All samples were compared on the same standard line plot.

The use of miniassay because of its accuracy, speed, and ease of use, has allowed for the assay of several hundred samples daily in the same assay. Accordingly, this assay has allowed for the analysis of the elution profiles from the P-200 column and the HPLC column with relative ease. Such a method of assay did not exist prior to the development of the miniassay described herein.

B. Suspension Assay. This assay is referred to as the suspension assay since it is designed to use cells which grow in suspension, that is cells which do not attach to the cell culture vessel surface. The preferred cell type is the Y-79 cell line (human retinoblastoma). However, this assay is not restricted to this cell type. Any cell type which (a) responds to UGIF by a decrease in cell growth and (b) grows in culture in a suspension mode, i.e., does not attach to the cell surface, may be used.

The cells were seeded at a density of $4 \times 10^4$ cells/ml/well of a 24 well tissue culture vessel (Falcon). Preferable growth medium is 90% RPMI basal media plus 10% calf serum and penicillin (100 units/ml) and streptomycin (100 ug/ml), however, any medium (including Bfs) which supports the growth of the cell line used would be acceptable. At the same time as seeding, the experimental samples were added at the appropriate levels to the seeding growth medium. The cells were allowed to incubate for 22 hours in a tissue culture incubator at 37° C. and 5% $CO_2$, [$^3$H]thymidine was added (2 μCi/ml), and cultures were allowed to incubate for another 2–3 hours. The contents of each well (medium and cells) were removed and incubated with an equal volume of 20% TCA for 1 hr. at 2° C. DNA precipitates were collected and radioactivity determined by addition of the precipitate to a Millipore filter manifold fitted with 2.4 cm glass fiber filters (934-AH, Watman). The filters were washed with 5 changes of ice cold ethanol (2 ml/well each wash). Each filter was removed from the manifold and added to a scintillation vial containing liquid counting scintillant. Counts per minute (cpm) were determined by scintillation counting.

The suspension assay allows assay of cells grown only in suspension such as the Y-79 cell line. This cell line has been valuable since it does not contain receptor for TGF-β growth factor. Accordingly, data described herein show that UGIF does not act through the TGF-β receptor system, at least with respect to the Y-79 cell line.

Both the miniassay and the suspension assay has allowed for the identification of UGIF in small aliquots and minialiquots simultaneously. These assays have allowed for the determination of UGIF in each step of the purification procedure described herein in the next example.

EXAMPLE 2

Purification of UGIF

Urogenital sinus (UGS) was removed intact from day 18 fetal rats. The UGS were placed in individual wells (1UGS per well) of 96 well tissue culture dishes (Linbro, McLean, Va.) in 300 μl of media Bfs and allowed to incubate for 48 hour segments. Each 48 hours the conditioned medium (CM) from each well was collected and frozen at −20° C. until used. There is no apparent loss of UGIF activity after CM freeze-thaw as compared to freshly collected CM. Organ cultures of UGS were maintained for several months in the 96 well dishes. Also used were the monolayer of cells which emanated from the periphery of the UGS explants. These cells appeared homogeneous and were fibroblastoid in appearance. These cells were identified as fibroblasts based on morphological appearance and identification of vimentin intermediate filaments. Upon subpassage, the fibroblast cells attained confluence approximately 1 week after passage. Through this point UGIF activity was not produced (or secreted into the growth medium) by the cultures. After approximately 3–4 weeks in culture the fibroblast monolayers produced multicellular spheroids which grew up from the monolayer of cells. At this point UGIF activity was produced by the spheroids (inferred from the data). Accordingly, CM media was collected each 48 hours from both the original UGS organ cultures and the spheroid cultures derived from the fibroblast monolayers. Studies have shown that approximately the same Units of UGIF activity (10–20

Units/ml) is produced by both UGS explants and spheroids, and that there are no apparent differences in UGIF properties derived from either source. Hence, CM from both sources were stored and used separately for the purification procedure described herein.

Figure 2:
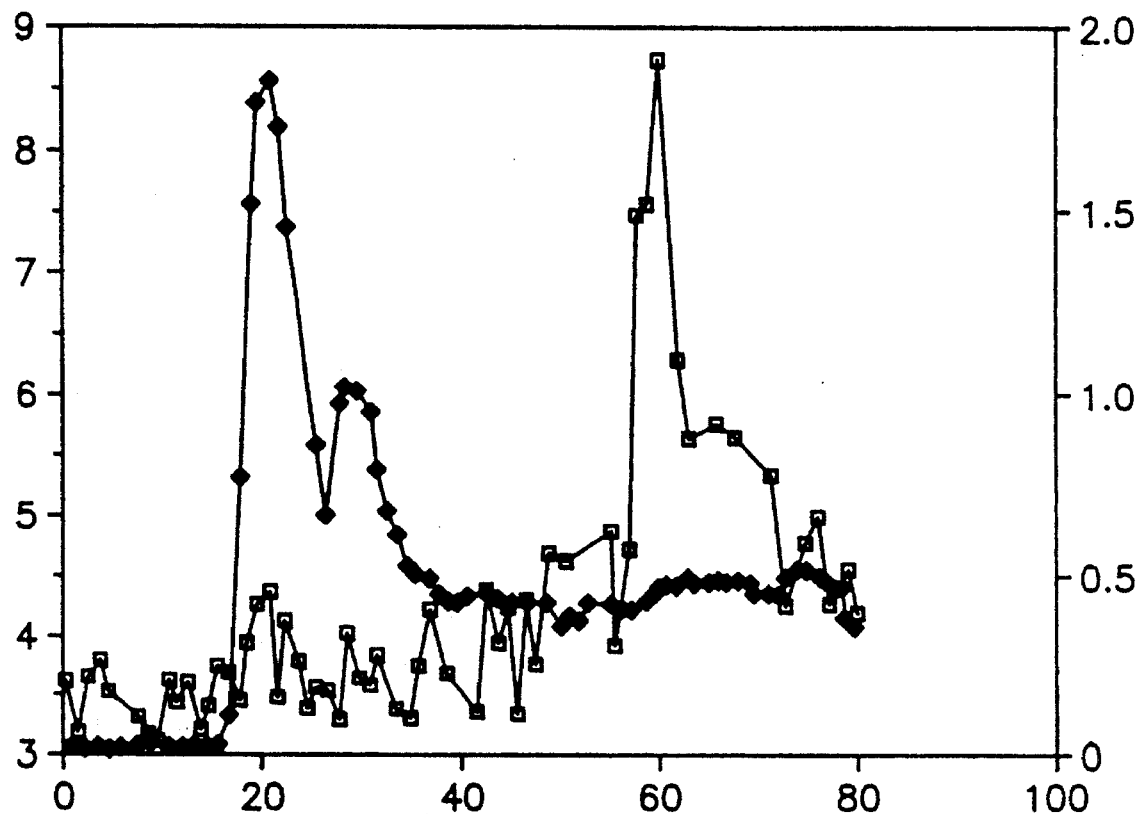
FIG. 2 demonstrates the elution profile of UGIF on a Bio-Gel P-200 column chromatography.
Figure 3:
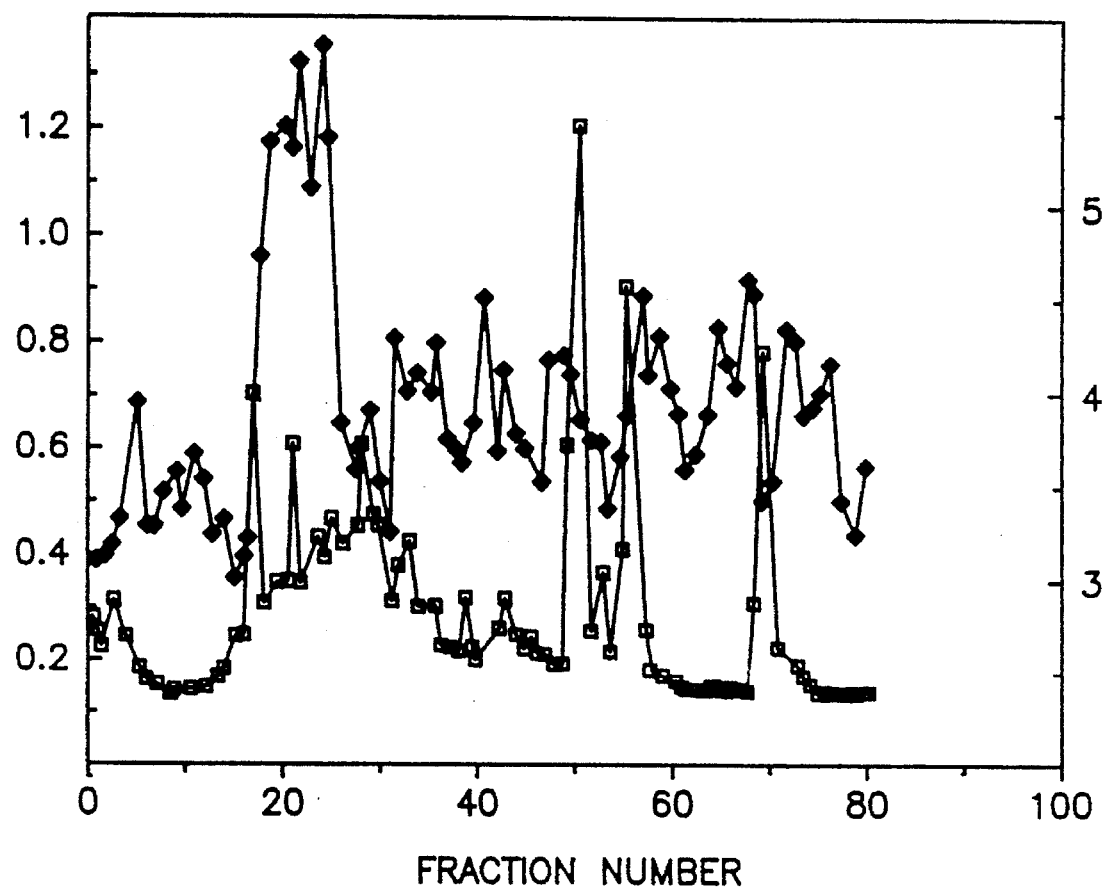
FIG. 3 demonstrates the elution profile of UGIF on a high performance liquid chromatography reverse phase column.

CM (150 ml) was next processed by dialysis versus 1M acetic acid (4 liters) for 24 hours at 4° C. using a Spectra/Por dialysis bag (Mr cutoff at 3500). The preferred acid is 1M acetic acid, yet any acid which does not lower the pH to less than about 2.5 would be acceptable for this step and any step using 1M acetic acid hereafter. The purpose of dialysis versus acid was to place UGIF in a state of solubility such that hydrophobic interactions with gel matrices or containers was minimized. The dialyzed CM was next centrifuged to remove precipitated protein and the soluble fraction (50 ml batches) were lyophilized to dryness. The lyophilized material (equivalent to 50 ml CM) was resolubilized in 1M acetic acid (3 ml) for 24 hours at 37° C. This material of 3 ml volume was added entotal to a 66×3 cm column containing Bio-Gel P-200 beads (Bio-Rad, Richmond, Calif., USA), equilibrated in 1M acetic acid. Although P-200 is the preferred resin, any gel filtration matrix which withstands acid conditions, such as any of the Sephacryl (Pharmacia, Piscataway, N.J., USA) matrix, would be usable. The column was eluted under a hydrostatic pressure of 75 cm $H_2O$ and 3.75 ml fractions were collected. Each of 80 fractions were assayed (100 µl/fraction) for UGIF activity using the miniassay as described herein. FIG. 2 demonstrates a typical elution profile of UGIF off the P-200 column. The peak of UGIF activity was pooled (Fractions #60–65) and lyophilized to dryness. The lyophilized material was resolubilized in 1% trifluoroacetic acid (2 ml) and injected into a Beckman high performance liquid chromatography system (Brea, Calif., USA) fitted with a $C_{18}$ reverse phase column and equilibrated in 30% acetonitrile. The column was eluted with a 30%–80% gradient of acetonitrile which elutes proteins retained by virtue of their hydrophobic properties. The column was eluted at 0.5%/ml/minute. Aliquots (100 µl) were assayed from each fraction using the miniassay as described herein. FIG. 3 demonstrates a typical elution profile of UGIF off the HPLC reverse phase $C_{18}$ column. The fractions containing UGIF were pooled (6 ml total volume) (fractions #18–24) and represented an approximate purification of 8000-fold. FIG. 1 demonstrates the flow diagram of one embodiment of the purification procedure and see Table II for the purification values of a typical preparation. The final yield of UGIF was a 67% recovery which represents approximately 30 µg of UGIF based on current estimates of molecular weight and starting concentrations in crude CM. The pooled fractions were lyophilized to dryness and stored at −20° C. until use, or for indefinite periods.

Figure 8A:
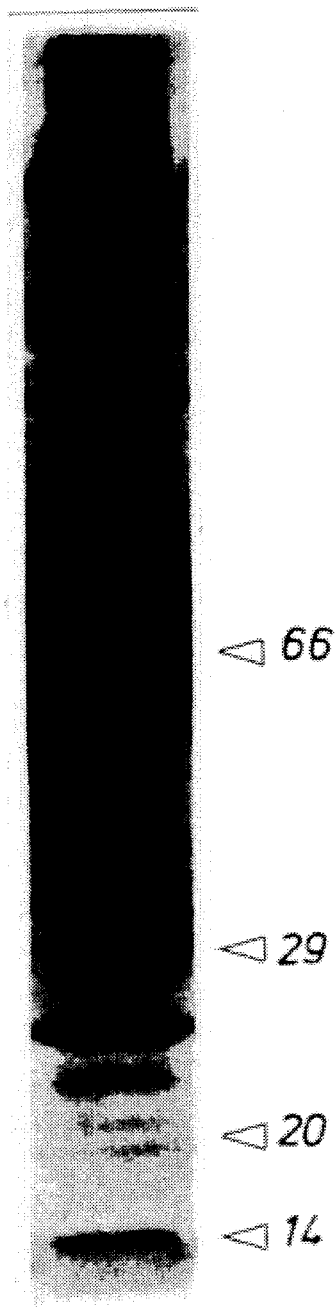
FIGS. 8A and 8B demonstrate a polyacrylamide gel electrophoretic profile of UGIF at different stages of purity.
Figure 8B:
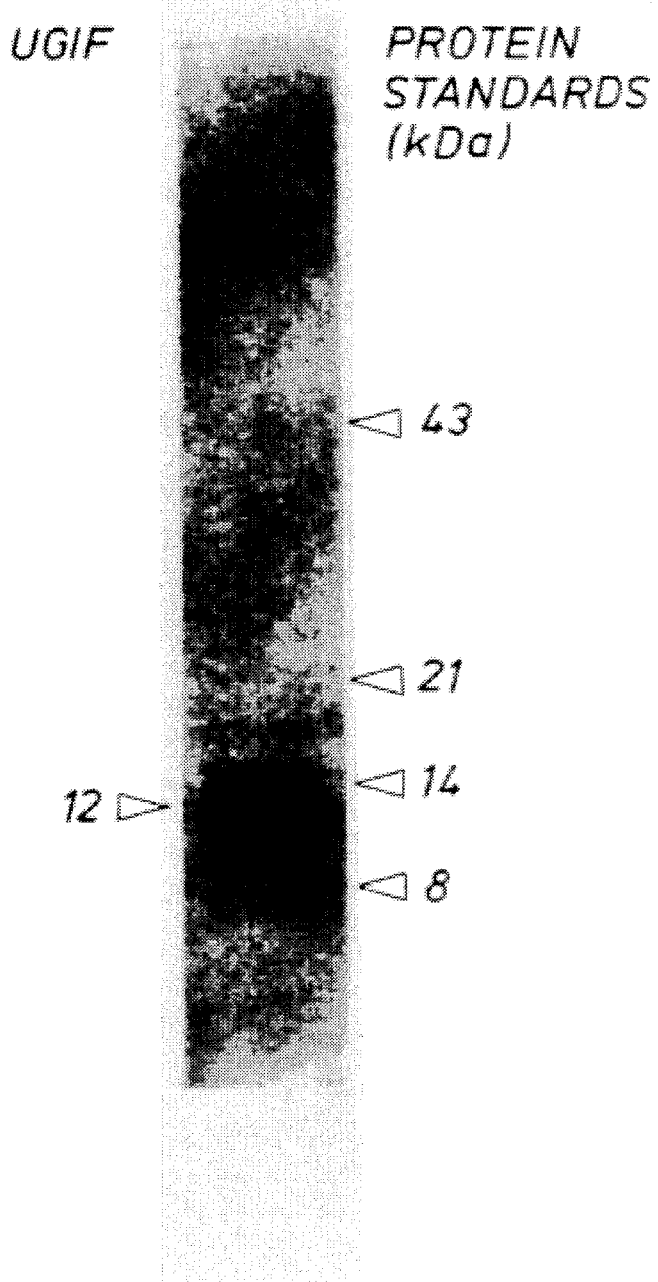

Aliquots were taken from each step of the purification procedure. Samples were prepared by lyophilization and resolubilized in Lammeli sample buffer (100 µl) without reducing agent. Samples were loaded onto 15% acrylamide gels and electrophoresed for 6 hours at 40–70 mAmp current. The gel was fixed in acetic acid-methanol and subsequently stained in Coomassi Brilliant Blue (Eastman, Rochester, N.Y., USA). FIG. 8 demonstrates the photographic representation of the polyacrylamide gel electrophoresis of the UGIF. FIG. 8A represents the starting material. FIG. 8B represents the material eluted off the HPLC column. Molecular weight markers are noted to the right of each gel lane.

EXAMPLE 3

Inhibition of Neoplastic cell growth by UGIF

NBT-II cells were seeded at a density of $5\times10^4$ viable cells per $cm^2$ in 24 well tissue culture plates in the presence or absence of 30% volume/volume ratio of UGS conditioned medium. At days 1, 2, 4, and 6 after plating, the cell number per well was counted with an improved Neubauer hemocytometer. For counting the cells were harvested by brief exposure to trypsin (2.5%) and EDTA (0.25%). The cell number/well in the control and experimental was determined and graphed for each time point. The cells responded by a change in cell number by day 2–4 and by day 6 represented a difference (inhibition of cell number by UGIF) of approximately 46% as demonstrated in FIG. 5. The alteration in cell number correlates well (but lags in time approximately by 48 hours) with the change in thymidine incorporation as can be seen and compared between FIGS. 5 and 4, respectively.

EXAMPLE 4

Inhibition of proliferation of Urogenital Sinus Fibroblast by UGIF

Primary cultures of fibroblasts (fibroblastoid appearing) cells were established from the monolayer of cells emanating from the periphery of the UGS organ explants. The organ explants were removed physically, and the primary fibroblasts were harvested by mild trypsinization (2.5%). The fibroblasts were seeded at a density of $5\times10^4$ cells/$cm^2$ in 24 well dishes. The cells were exposed to CM (30%) and control medium. The cultures were analyzed for incorporation of tritiated thymidine incorporation in a fashion identical to that described for the miniassay described previously. The thymidine incorporation was inhibited by approximately 50% when these cells were exposed to CM (containing UGIF bioactivity). See Table II.

EXAMPLE 5

Alteration in cell phenotype by UGIF

NBT-II cells were plated as those described in Example 3. The cells were exposed to CM (30% for 24 hours and certain wells contained 10 µCi/ml of [$^{35}$S]methionine. Control and experimental wells were photographed and then extracted with a buffer including sodium dodecyl sulfate and urea. The growth medium was saved and proteins were precipitated from it with exposure to 10% TCA, 4° C. for one hour. The precipitated proteins were harvested by filtration on glass-fiber filters, the filters washed extensively with ETOH and then scintillation counted. The cell monolayer extract was prepared and analyzed in an identical fashion. As shown in FIG. 4, when cells were exposed to UGIF, the secretion of newly synthesized proteins was increased by approximately 20%. In addition, the cells assumed a morphology not typical of epithelial cells. As shown in FIG. 7, the cells exposed to UGIF demonstrated filopodia and lamellipodia (cellular extensions) and were more spread out in their appearance as compared to the typical epithelioid appearance of the control cultures. These results show that not only does UGIF affect the growth rate of cells, it also affects phenotypic properties of cells, i.e., the differentiated state of cells.

EXAMPLE 6

U4F Mesenchymal Cell Line

The development of a U4F mesenchymal cell line, U4F spheroids, and U4F1 cell strain are described in Rowley, D. R., In Vitro Cell. Dev. Biol. 28A: 29–38 (1992), which is incorporated herein by reference.

U4F Cell Lines. A cell monolayer with fibroblastlike morphology which emanated from UGS organ cultures was established. UGS organ cultures (See Example 2) were mechanically lifted from cell culture plates, and the remaining monolayer was subcultured. At successful subculture, the cells were termed the U4F (urogenital sinus organ culture series 4, fibroblastlike morphology) cell line. Typical fibroblastlike features included a pointed or spindle shape with multiple lamellipodia and filopodia. At higher density, sheets of elongated and pointed cells were observed, typical of fibroblastoid cell types. Immunocytochemical analysis indicated that the U4F cells contained a vimentin intermediate filament content, and were negative for desmin and cytokeratins 8, 18, and 14. These data, together with a fetal tissue origin, confirm a mesenchymal designation for the U4F cell line. The U4F cell line has been subpassaged and cultured continuously for 2 years without change in characteristics and has accordingly been designated a continuous cell line.

U4F spheroid formation. At near-confluent densities U4F cells exhibited typical plateau-phase growth characteristics. Confluent monolayers survived for several weeks (culture medium changed every 48 hours) with slight increases in cell density. Approximately 3 weeks after reaching confluence (days 25 to 27), spontaneous aggregation of cells produced several foci (approximately 5 foci/cm$^2$) of localized high cell density. The foci increased in size and evolved into multicellular spherical masses (spheroids) eventually reaching 1 to 3 mm in diameter. The U4F spheroids were stable for several months in culture and could be mechanically lifted and transplanted to new plates, where they would attach and yield a monolayer outgrowth of cells. Small spheroids consisted of cell masses, with a lower cell density (lower cell-to-matrix ratio) in the central core, and often two cell masses were connected by cellular bridges. Later stage spheroids consisted of a cellular capsule (one to three cell layers) of fibroblastlike cells surrounding a matrix core. Spheroid cores consisted of an eosinophilic matrix containing a few cell nuclei. Secondary aggregations of cells developed from the spheroid capsule in later stages and produced a secondary spheroidal mass. In later stage spheroids this pattern of development generated a lobulatedlike appearance with irregular septa separating secondary regions of spheroid formation.

U4F1 cell strain. Upon passage of a plate of long-term, confluent U4F spheroids (8 months) a monolayer arose spontaneously in one newly seeded plate which maintained a stationary growth phase at confluent density and did not develop spheroids. This alteration in cell property was maintained in subsequent passages. In addition, individual cells seemed larger and more spread out. Immunocytochemical analysis showed positive for vimentin intermediate filament content and negative for desmin and the cytokeratins, indicating a mesenchymal designation. The network of vimentin intermediate filaments in these cells was more developed and dense in contrast to parent U4F cultures. Owing to the combined changes in specific properties relative to the parent cell line, this strain was termed the U4F1 cell strain. These properties have remained stable during continuous subculture of the U4F1 cell strain for approximately 2 years and spheroid formation has not been detected.

Figure 9:
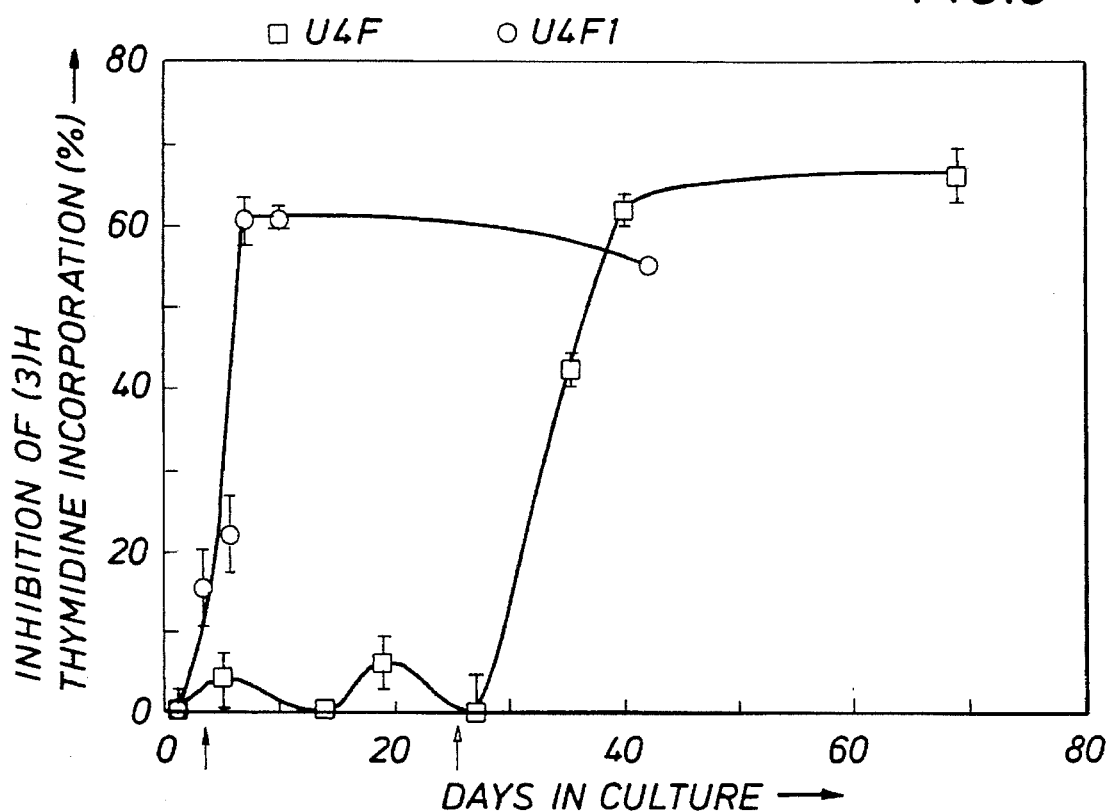
FIG. 9 shows the time course of UGIF activity production by U4F and U4F1 cell cultures.

Secretion of UGIF activity. To compare with previous studies using urogenital sinus organ cultures, conditioned media from the U4F cell line and the U4F1 cell strain were assayed for expression of negative growth activity (UGIF activity). UGIF activity was functionally defined as that activity producing a 50% inhibition of [$^3$H]thymidine incorporation (relative to control) in Mv-Lu-1 cells under the assay conditions as described in Example 1. The time course of UGIF activity production by U4F and U4F1 cultures is shown in FIG. 9. U4F cells reached confluence 4–5 days after seeding (FIG. 9, closed arrow). UGIF activity was not detected in preconfluent or confluent U4F cultures without spheroids. Spheroid formation (visible mass, 150–250 μm diameter) was observed at approximately 28–30 days of culture (open arrow, FIG. 9). UGIF activity was first detected concurrent with visible formation of spheroids at approximately 30 to 35 days of culture. In addition, spheroids could be mechanically lifted and transplanted to new plates where UGIF activity was detected in the first collection (48 hours) of conditioned media. Spheroids could be enzymatically dissociated by exposure to trypsin-EDTA and cells replated. In these cultures, spheroids formed coordinate with expression of UGIF activity in the time frame observed previously (28 to 35 days). In all U4F cultures, expression of UGIF activity was restricted to plates containing spheroids. Spheroids could be cycled through unsupplemented (serum-free) DMEM medium (changed daily), and UGIF activity was expressed for up to 5 to 7 days, at which time cultures degenerated.

In contrast to U4F cells, the U4F1 cell strain expressed measurable UGIF activity immediately after seeding (FIG. 9). UGIF activity increased and reached constant levels at confluency. Expression of UGIF activity in conditioned medium was maintained by confluent U4F1 monolayers for several weeks before passage. Unlike U4F cells, U4F1 cultures typically transformed growth characteristics after 8 to 10 weeks of culture (in original plate) and initiated density-independent proliferation from the stationary phase, exhausted nutrients, and reached culture decline phase (cell death). In contrast, UGIF activity has been harvested from U4F spheroids for up to 9 months of continuous culture in original plates.

Conditioned medium from U4F spheroids (50 ml) was dialyzed against 1M acetic acid for 18 hours, lyophilized, and resolubilized in 1.0 ml of 1M acetic acid and applied to a Bio-Gel P-200 column equilibrated in 1M acetic acid (27° C.). Aliquots (100 μl) from each fraction were vacuum dried, resolubilized in medium Bfs (65 μl) and assayed for inhibition of [$^3$H]thymidine incorporation using the miniassay procedure as described in Example 1.

EXAMPLE 7

Modified Purification Procedure for UGIF obtained from U4F spheroids or U4F1 cells.

UGIF activity is purified from conditioned media (collections each 48 hr) from U4F spheroid cultures in serum-free, chemically-defined medium. A serum-free, chemically-defined medium was developed empirically, based on the parameters of cell viability and relative growth rates. Chemically-defined medium consisted of MCDB-110 basal media (Sigma, St. Louis, Mo., USA) supplemented with insulin (5

μg/ml), transferrin (5 μg/ml), selenium (5 ng/ml), (each from Sigma) and epidermal growth factor (EGF; 0.1 μg/ml) (UBI, Lake Placid, N.Y., USA and Collaborative Research, Lexington, Mass., USA), and testosterone (0.5 μg/ml) (Sigma, St. Louis, Mo., USA).

Collected conditioned media is stored at −20° C. until time of use and thawed at 37° C. Proteins are precipitated from 600 ml of conditioned media by addition of solid ammonium sulfate. The proteins precipitated from the 0–20% saturation are discarded. Proteins precipitated from the 20–45% saturation of ammonium sulfate are collected by centrifugation.

The pelleted protein is solubilized in 72 ml of 20 mM ammonium carbonate buffer, pH 8.85 and dialyzed (Spectra/Por #3 bag, 3,500 MW cutoff) against 8 liters of this buffer, for a period of about 16–18 hours at 4° C.

The dialyzed material is applied and chromatographed through a DE-52 ion exchange column (Whatman, Maidstone, UK) anionic exchanger (1.5×14 cm), washed with 45 ml of the same buffer and eluted with a linear gradient of ammonium carbonate buffer, pH 8.85 (20 mM to 300 mM).

The eluted region assaying positive for UGIF activity (conductivity range 14.5–19 mS/cm, Conductivity Meter, Radiometer, Copenhagen, Denmark) is collected (approximately 20–25 ml) and dialyzed vs 1M acetic acid (2 liters) for a period of about 16–18 hours at 4° C. The dialyzed material is quick frozen in a methanol-solid $CO_2$ bath and lyophilized and stored at 4° C. until used next. For the next step, lyophilized material is resolubilized in 1 ml of 1M acetic acid, pH 2.5 and chromatographed through a Bio-Gel (Bio-Rad, Richmond, Calif., USA) P-100 gel filtration column (1.5×93 cm) equilibrated in 1M acetic acid. Each fraction is assayed for growth inhibitory activity (inhibition of [$^3$H]thymidine using the PC-3 cell Miniassay procedure) and the region of bioactivity is collected and vacuum dried using a Savant Speed-Vac system (Savant Instruments, Farmington, N.Y., USA).

The material from gel filtration chromatography is resolubilized in 500 μl of 50% formic acid and chromatographed through a reverse phase C-18 HPLC column. The sample is loaded and the acetonitrile concentration brought from 0–30% in 5 minutes, then the column eluted with a shallow linear gradient of 30–70% acetonitrile at 0.25%/minute/ml. The primary peak of activity associated with the p18–20 kiloDalton protein (approximately 34–36% acetonitrile) is pooled, and lyophilized. Activity is determined by the inhibition of [$^3$H]thymidine incorporation into DNA using PC-3 cells as targets with the Miniassay procedure of Example 1A. Based on SDS-PAGE analysis of each fraction, this material is substantially pure UGIF activity (approximately 90% pure).

EXAMPLE 8

UGIF Administered to Nude Mice

The basic procedure involves the injection of human prostatic PC-3 carcinoma cells into male Balb/c nu/nu "nude" mice (Teconic, Germantown, N.Y., USA) and a determination of the affects of substantially pure UGIF on the tumorigenicity of these cells in vivo. The PC-3 cells were cultured in vitro, harvested, and resuspended in a Matrigel vehicle (Collaborative Research, Bedford, Mass., USA). The protocol for injecting PC-3 cells in Matrigel is based on the procedures published by Pretlow et al., Cancer Research 51: 3814–3817, 1991, and incorporated herein by reference, using PC-3 and other prostatic cell lines, although other protocols may be used. These studies have shown an enhanced tumorigenicity of the carcinoma cells when they are prepared and injected in Matrigel.

Matrigel preparations were made either with or without UGIF (HPLC-purified and vacuum dried in acetonitrile) following the procedure as outlined below. The lyophilized HPLC-purified UGIF material was solubilized in 100 μl Bfs medium. The preparation was added to 100 μl of Matrigel and incubated for about 2.5 hours at 2°–4° C. The control was vacuum dried acetonitrile (vehicle control), and otherwise prepared identically to the UGIF-containing preparation. PC-3 cells were harvested and 1×10$^6$ cells prepared in 100 μl of PC-3 cell medium (DMEM-F12 93%, fetal calf serum 7%, penicillin 100 units/ml and streptomycin 100 μg/ml) and mixed with 100 μl Matrigel. The cells-Matrigel preparation were mixed with the UGIF-Matrigel preparation and the final volume (400 μl) injected subcutaneously into the lateral flanks of male Balb/c nu/nu mice. Three (3) mice were injected subcutaneously in the lateral flanks with each mouse receiving control preparations on one side (minus UGIF) and UGIF-containing preparations (approximately ½ maximal activity as determined by in vitro activity) on the contralateral side for direct comparison. Mice were observed for a period of 7 days and monitored for the development of palpable tumors. Prior to the development of morbid tumors, the mice were euthanized and tumors excised. The diameter, volume and wet weight were recorded. Results are shown in Table III.

TABLE III

| In Vivo Effects of UGIF on Tumor Growth (PC-3 human prostatic carcinoma cells) | | |
| --- | --- | --- |
| Tumor Diameter (mm) | Tumor Volume (cubic mm) | Tumor wet Weight (mg) |

| | Tumor Diameter (mm) | Tumor Volume (cubic mm) | Tumor wet Weight (mg) |
| --- | --- | --- | --- |
| Control | 9.34 ± 0.55 | 435.00 ± 78.45 | 196.63 ± 21.80 |
| UGIF Treated | 7.33 ± 0.36 | 209.55 ± 31.31 | 158.17 ± 17.68 |

Results are expressed as the mean ± S.E.M. (Standard Error of the Mean).

EXAMPLE 9

Figure 10:
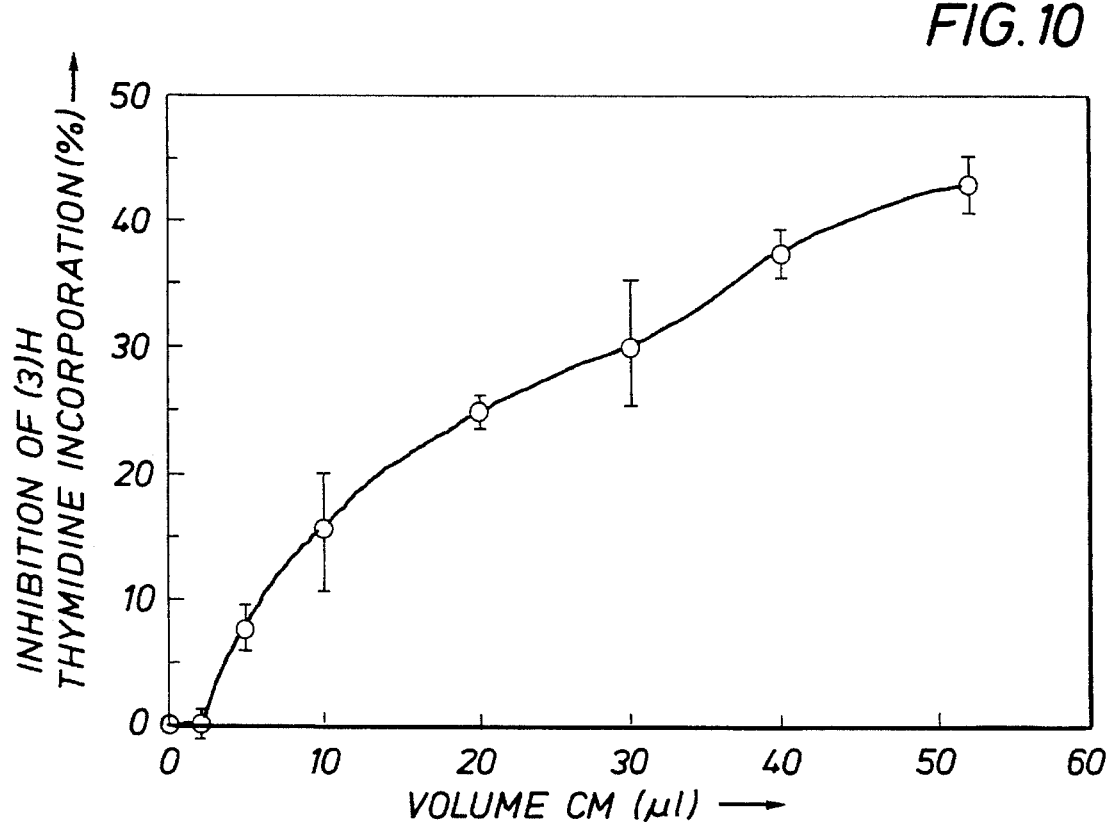
FIG. 10 shows the % inhibition, [$^3$H]thymidine incorporation in rat urogenital sinus (RUGS) cells using crude conditioned medium.
Figure 11:
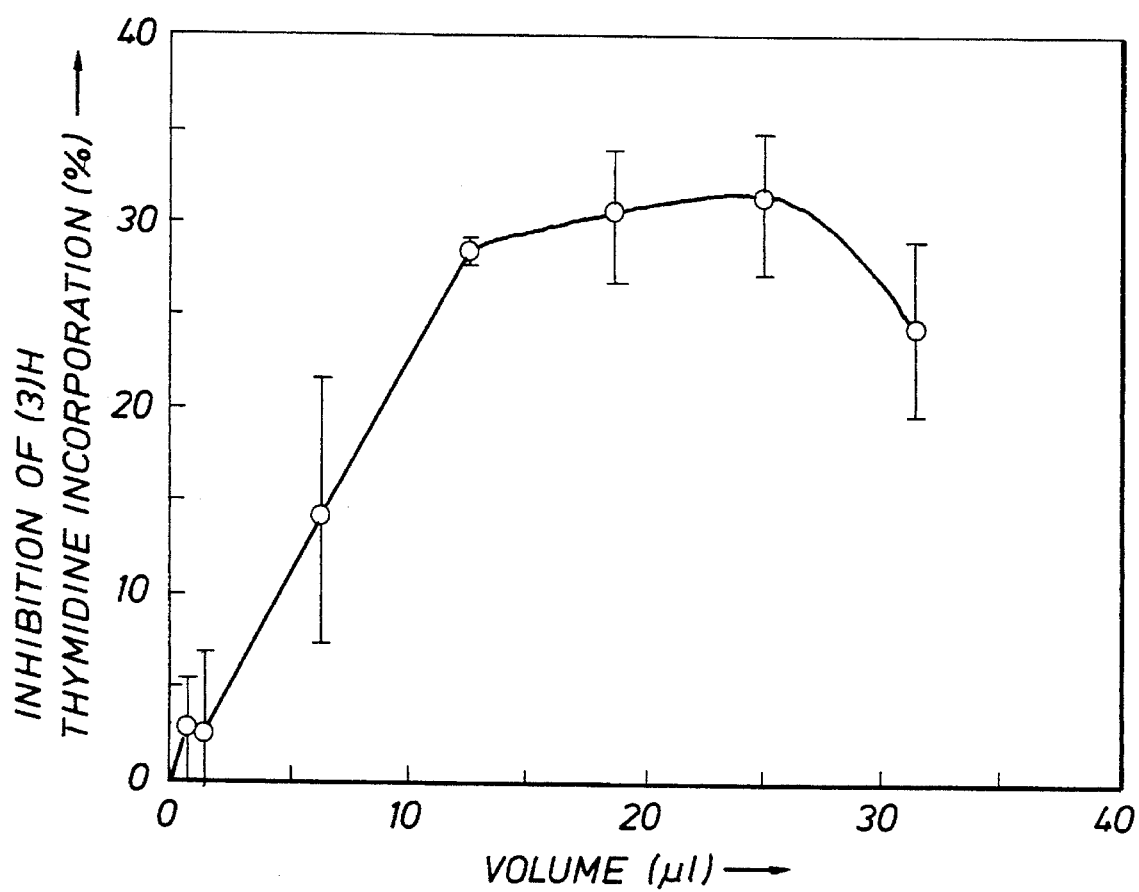
FIG. 11 shows the % inhibition, [$^3$H]thymidine incorporation in RUGS cells using partially purified UGIF from U4F spheroids.

Crude conditioned medium and partially purified UGIF purified from U4F spheroids (P-200 eluate) was solubilized in growth medium and added in increasing concentration to cultures of normal rat urogenital sinus stromal cells (RUGS) in 96-well plates. The miniassay procedure (Example 1) was used for determination of [$^3$H]thymidine incorporation. Results, depicted in FIGS. 10 (CM) and 11 (partially purified UGIF), show that UGIF inhibits [$^3$H]thymidine incorporation, showing an effect of UGIF on cells taken from near primary explants of normal urogenital sinus cells.

Having now fully described this invention, it will be appreciated by those skilled in the art that the same can be performed within a wide range of equivalent parameters of composition, conditions and modes of administration without departing from the spirit or scope of the invention or of any embodiment thereof.

What is claimed is:

1. A pharmaceutical composition comprising urogenital sinus derived inhibitory factor having an activity of at least 1 as measured by the UGIF units assay test, being substantially free of albumin and being about 70–8000 fold enriched in UGIF activity over tissue per dry weight of tissue.

2. A composition according to claim 1 having a molecular weight of about 10,000–20,000 Daltons.

3. A method of suppressing the growth of prostatic cancer cells in vivo, which comprises contacting said prostatic cancer cells with a growth suppressing amount of the UGIF composition of claim 2.

4. A method of treating neoplastic disease in an individual by suppressing the growth of prostatic cancer cells, comprising administering to said individual a cell differentiating amount of the composition of claim 3.

5. A pharmaceutical composition comprising urogenital sinus derived inhibitory factor, having a molecular weight of about 10,000–20,000 Daltons, retaining biological activity and acid stability following treatment at 80° C. for 10 min., wherein said composition inhibits the growth of Y-79, A-549, Mv 1 Lu, NRK, NBT-11 and Hela cells.

6. A pharmaceutical composition comprising urogenital sinus inhibitory factor having a specific activity greater that 70 units per mg protein.

* * * * *

UNITED STATES PATENT AND TRADEMARK OFFICE
CERTIFICATE OF CORRECTION

PATENT NO. : 5,496,800
DATED : March 5, 1996
INVENTOR(S) : David R. Rowley

It is certified that error appears in the above-indentified patent and that said Letters Patent is hereby corrected as shown below:

Column 1, line 9, add --The invention was made with Government support and the Government has certain rights in the invention.--

Signed and Sealed this

Twenty-seventh Day of August, 1996

*Attest:*

BRUCE LEHMAN

*Attesting Officer*  *Commissioner of Patents and Trademarks*